(12) United States Patent
Teich et al.

(10) Patent No.: US 6,537,231 B1
(45) Date of Patent: Mar. 25, 2003

(54) DETECTION OF INFLAMMATORY PROCESSES AND MALIGNANCIES IN MAMMALS

(76) Inventors: Sorin Teich, Ha-hadarim Street 4, Savion (IL), 56534; Eli Eliav, Ephraim Street 480a, Givat Zion, Ashkelon (IL), 76587

(*) Notice: Subject to any disclaimer, the term of this patent is extended or adjusted under 35 U.S.C. 154(b) by 0 days.

(21) Appl. No.: 09/719,785
(22) PCT Filed: Jun. 21, 1999
(86) PCT No.: PCT/IL99/00337
§ 371 (c)(1), (2), (4) Date: Feb. 19, 2001
(87) PCT Pub. No.: WO99/66838
PCT Pub. Date: Dec. 29, 1999

(30) Foreign Application Priority Data

Jun. 22, 1998 (IL) .................................................. 125053

(51) Int. Cl.[7] .................................................. A61B 5/05
(52) U.S. Cl. ........................................ 600/554; 600/547
(58) Field of Search ................................. 600/554, 546, 600/547, 587–595

(56) References Cited

U.S. PATENT DOCUMENTS

| | | | | |
|---|---|---|---|---|
| 4,644,959 A | * | 2/1987 | Calmanovici | 128/733 |
| 4,817,628 A | * | 4/1989 | Zealear et al. | 128/741 |
| 5,549,656 A | * | 8/1996 | Reiss | 607/48 |
| 6,132,387 A | * | 10/2000 | Gozani et al. | 600/554 |
| 6,379,313 B1 | * | 4/2002 | Gozani et al. | 600/554 |
| 2002/0026123 A1 | * | 2/2002 | Pearlman | 600/547 |

* cited by examiner

Primary Examiner—Joseph Pelham
(74) Attorney, Agent, or Firm—Mayer, Brown, Rowe & Maw

(57) ABSTRACT

The detection of inflammatory processes and malignancies in the human body is based on controlled assessment of sensory changes in the peripheral nervous system by a) comparing the detection thresholds for electrical stimulation in a suspected location and in its homological contralateral location, or by b) measuring the difference between thresholds at two areas in the body, innervated by different nerves and re-measuring the same difference after at least one time interval. The sensitivity threshold for electrical stimuli is obtained by 3 steps: a) attaching electrodes that are connected to an electrical pulse generator, to the skin (or mucosa) adjacent to tested area, b) applying a train of electrical pulses of varying intensities through these electrodes, c) collecting the subject's responses (yes/no) and processing the collected data to obtain the sensitivity threshold.

13 Claims, 3 Drawing Sheets

DETECTION OF INFLAMMATORY PROCESSES AND MALIGNANCIES IN MAMMALS

FIELD OF THE INVENTION

Figure 1A:
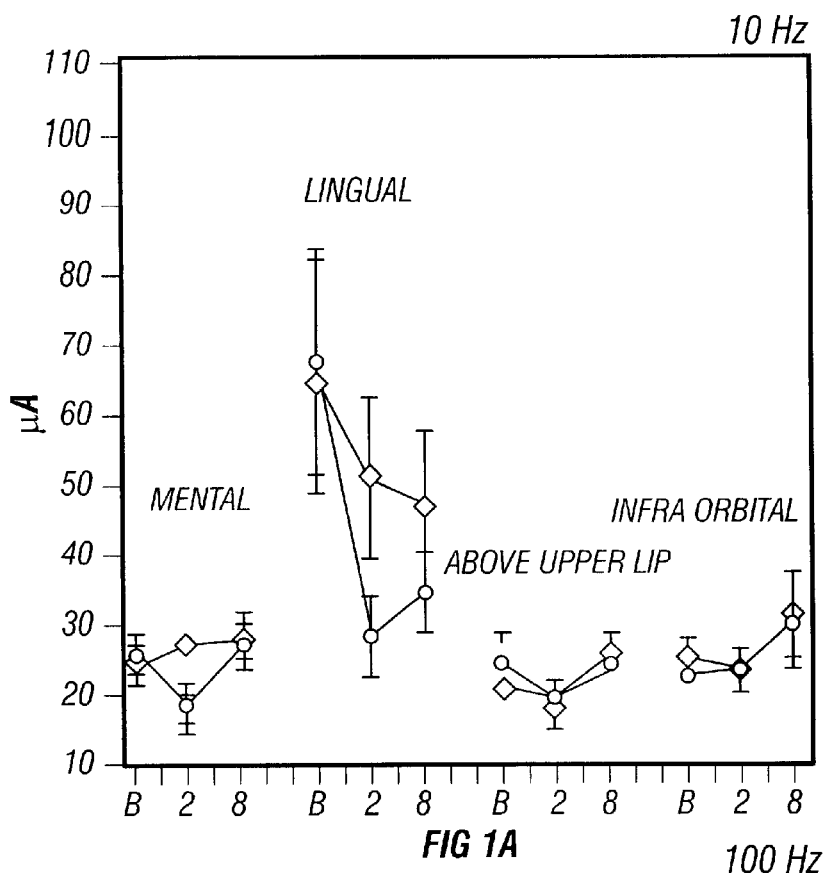
Figure 1B:
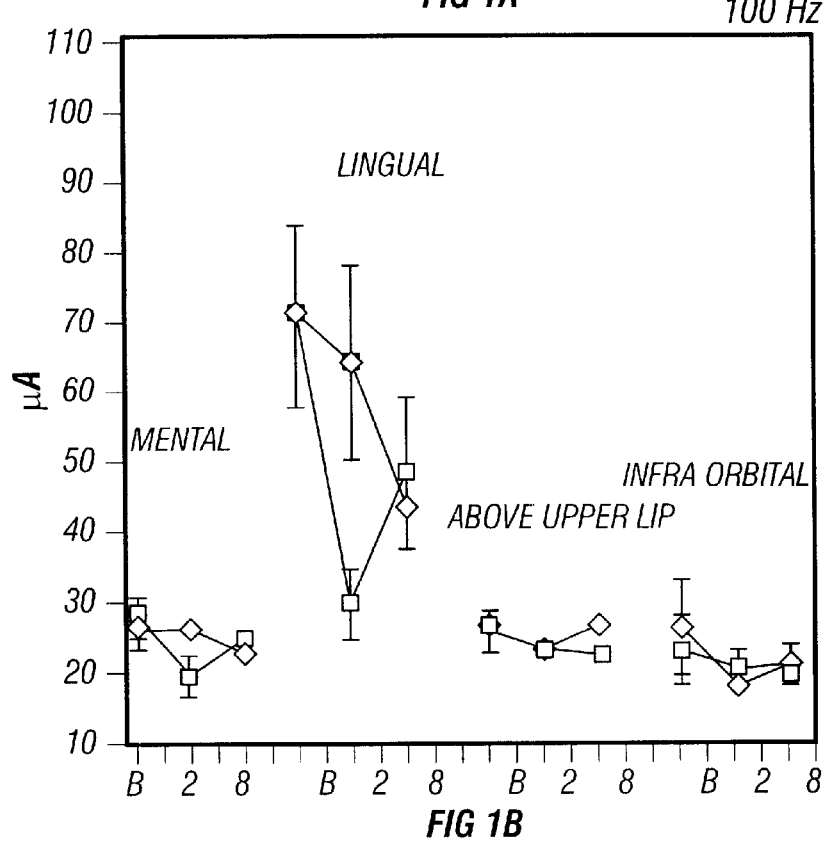
Figure 1C:
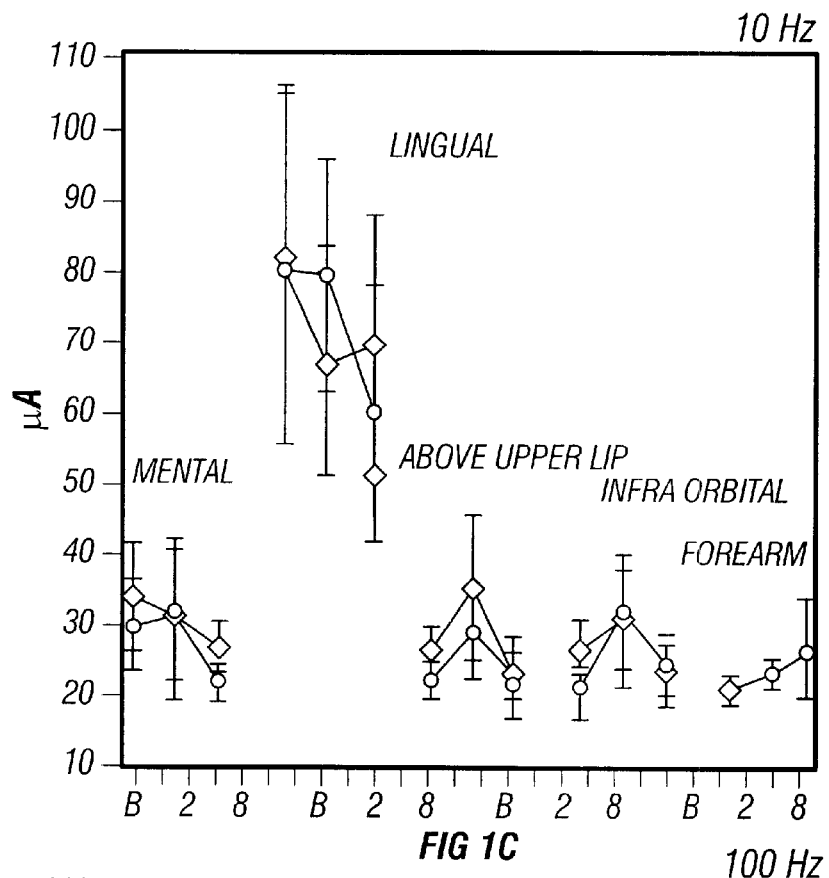
Figure 1D:
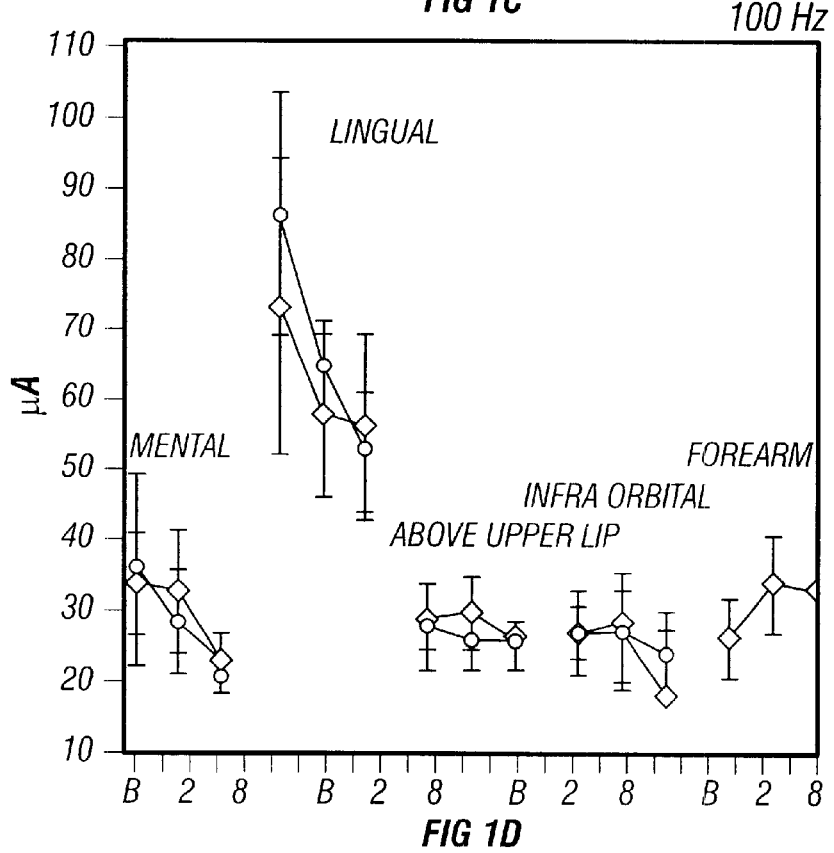

The present invention relates to a method for early detection of inflammatory processes and malignancies in the human body and for the detection of stress fractures in mammals' legs. More specifically, the said method is based on the detection of sensory changes in the peripheral nervous system wherein said changes are detected (a) by comparing the detection thresholds for electrical stimulation in the vicinity of a suspected site and in its homological contralateral site and/or (b) by measuring the difference between the detection thresholds for electrical stimulation in two different nerve territories and re-measuring the said difference after, at least, one time interval. A difference of more than 20% between the two corresponding thresholds of (a) or a change of more than 20% in the difference described in (b), indicates a higher probability of malignancy and/or inflammatory process.

BACKGROUND OF THE INVENTION

Pathological conditions are often accompanied by alternations in sensory function. These changes can vary from subtle changes to dramatic changes such as mechanical allodynia, cold allodynia, thermal and mechanical hyperalgesia and hyperpathia. There is an increasing recognition that systematic assessment of sensory response by controlled painful and nonpainfull stimulation can elucidate peripheral and central mechanisms and greatly aid in diagnosis and possibly in evaluation of treatment efficacy.

In case of malignancy there is an accumulating evidence that malignancy causes spontaneous sensory changes and that in many cases, neurological symptoms precede cancer diagnosis. For example, various paraneoplastic neurological syndromes have been described in association with malignancies but most often with small cell lung cancer and lymphomas (Khouatra et al, Rev. Med. Interne 18, (1997), p. 652–656), Hughes et al. showed that cancer can cause peripheral neuropathy (Hughes et al. *J Neurol.* 243 (1996) p. 371–376). This can be explained in light of the fact that malignancy can secrete or lead to secretion of substances that may cause clinical spontaneous neurological signs.

Malignancy is always accompanied by local inflammatory processes from its early stages, well before there is any clinical manifestation of inflammation or any other symptoms. On the other hand, it has been shown that inflammatory processes along the nerve trunk or adjacent to free nerve endings and receptors, alters the consequence of activity mainly in large-diameter primary afferents. For example, it has been shown that inflammation along the sciatic nerve in the rat increased the pain sensitivity to mechanical and thermal stimulation of the nerve target organ, the rat paw. (Eliav et al, *Society for Neuroscience Abstracts,* 23 (1997) p. 163)). It was also shown that inflammatory processes adjacent to free nerve endings and receptors increased the pain sensitivity to electrical stimulation (for example, A. J. Mannes et al, abstract in the 1997 annual meeting of the Society for Neuroscience, 597.12, p. 1527).

Unlike thermal or mechanical stimulation, electrical stimulation may bypass receptors and directly stimulate primary afferent axons. Therefore, changes in the electrical detection threshold can be measured prior to any other notable symptoms and can be assessed even in the presence of only minor inflammation response. Add to the above the fact that premalignant lesion transformation to malignant lesion is accompanied with enourmous accumulation of inflammatory millieu and hence, reduction in electrical detection threshold may serve as an early sign for aggravation of premalignant process into a malignant process. This neurological phenomenon is not to be mistakenly understood as paraneoplastic syndrome; the paraneoplastic syndrome is a spontaneous clinical sign that denotes a remote effect of the malignancy on the neural system whereas the subject of this patent is the fact that malignancy locally and sub clinically has an effect on the nerves that are in its vicinity. This effect can be detected by electrical stimulation of the target organ innervated by the affected nerve.

The present invention is a method for detecting localized malignancy by controlled assessment of changes in the sensory system even in their very first stages, prior to spontaneous symptoms. It takes advantage of the great sensitivity of the electrical detection threshold and instead of relying on spontaneous symptoms, utilizes this sensitivity to detect sensory changes in the periphery of possible malignancy, in a controlled way. The present invention is therefore, a quantitative and objective diagnostic tool for malignancies and inflammatory processes in their very first stage.

The controlled detection of sensory changes is done by comparing the electrical stimulation thresholds of a suspected lesion or area and its contralateral region in the body. For example, a suspected area on the skin will be tested against the identical site on the other half of the body, a breast cancer will be checked by comparing the sensitivity thresholds of equivalent regions of the two breasts and so on. A big difference between the two thresholds indicates suspicion of pathology.

Another way for a controlled detection of sensory changes is by obtaining the electrical stimulation thresholds at two different areas of the body, innervated by different nerves, as a routine check up procedure. At different areas, innervated by different nerves, a difference between the thresholds is expected, but if this difference shows a big change over time, there is a higher probability for pathology.

Different abnormal tissue detecting devices, such as those disclosed in U.S. Pat. Nos. 4,537,203, 4,955,383, 5,143,079 and EP 94307996.2, also consist of electrodes as part of their apparatus and method, but the method of detecting pathology disclosed in these patents is completely different from ours. The methods disclosed in the above mentioned patents relay on measuring physical parameters of tested tissues: the impedance (U.S. Pat. No. 4,537,203), the gradient of electrical activity (U.S. Pat. No. 4,955,383), the dielectric constants and/or conductivity (U.S. Pat. No. 5,143,079) or the physical response to various electromagnetic stimuli (EP 94307996.2). The method disclosed in our invention, in contrast to the above mentioned methods, is based on measuring physiological parameters. It is based on the detection of sensory changes by converting the subjective patient's responses to electrical stimuli into an objective parameter, i.e. the electrical stimulation detection threshold. Furthermore, by comparing different regions in same body and since we deal with physiological parameters, we have an internal calibration and there is no need for any calibration procedure of the device that is an essential process in the above mentioned patents. The internal calibration according to the present method, eliminates the need to calibrate the apparatus and even more important eliminates the need for a prior knowledge of normative values. This not only simplifies the method but has the advantage of a method which is sensitive to the individual subject under examination and to its specific condition.

SUMMARY OF THE INVENTION

The present invention relates to a method for the detection of inflammatory processes and malignancies in the human body based on controlled assessment of sensory changes in the peripheral nervous system by a) comparing the detection thresholds for electrical stimulation in a suspected location and in its homological contralateral location, or by b) measuring the difference between thresholds at two areas in the body, innervated by different nerves and re-measuring the same difference after at least one time interval.

The sensitivity threshold for electrical stimuli is obtained by 3 steps: a) attaching electrodes that are connected to an electrical pulse generator, to the skin (or mucosa) adjacent to tested area b) applying a train of electrical pulses of varying intensities through these electrodes c) collecting the subject's responses (yes/no) and processing the collected data to obtain the sensitivity threshold.

A difference between the thresholds at 2 contralateral sides of more than 20%, or a change over time in the difference between thresholds of adjacent areas of more than 20%, is indicative of malignancy or any other medical entity capable to cause occult localized inflammation along the track of the sensory nerve that innervates the checked target organ.

Furthermore, the present invention relates also to the detection of stress fractures in the limbs of racing horses and racing dogs wherein the method is the same as disclosed above and wherein the animal's response to stimulation is considered positive when the animal lifts up its tested leg in response to the electrical stimulation.

DETAILED DESCRIPTION OF THE INVENTION

The present invention relates to a method for the detection of inflammatory processes and malignancies in the human body.

The method according to said invention is based on the fact that localized inflammatory processes are accompanied by sensitivity changes in the peripheral nervous system. These changes can be detected by comparing the electrical detection thresholds in the vicinity of a suspected site and in its homological contralateral site, or by measuring the difference between the electrical detection thresholds at two different nerve territories at predetermined time intervals as a routine check up procedure or at arbitrary time intervals determined by casual visits, where time intervals can be a few weeks, months or years.

Furthermore, the present invention relates also to the detection of stress fractures in the limbs of racing horses and racing dogs. Bones fractures are known to be accompanied by inflammatory processes and it is also known that in response to electrical stimulation applied to a dog's or horse's leg, the animal lifts its leg. Stress fractures in racing animals' limbs are a common problem. The present invention is a relatively simple way for the diagnosis of such fractures. In human tested for bone stress fracture the detection threshold may be reduced.

The present invention will be further clarified and exemplified in detail by the following experiments:

EXPERIMENT 1

Sensory Tests Following Tooth Extraction

The consequence of post injury inflammation following extraction of a single, unilateral lower third molar tooth in humans have been studied by extensive bilateral sensitivity evaluations. The sensitivity evaluation have been performed in the territory of nerves assumed to be exposed to:

a) both inflammation and mechanical trauma (the inferior alveolar nerve).

b) inflammation with minimal or no trauma at all (the lingual nerve).

c) only the central consequences of peripheral inflammation (the infraorbital nerve).

Testing methods for sensory evaluation included heat and cold detection and pain thresholds, detection and pain threshold to 10 and 100 Hz electrical stimuli and detection threshold to mechanical stimuli.

Following are the methods and results of this study with emphasis on electrical stimulation tests:

Methods 12 patients and 6 control subjects were included in the study.

Patients were examined carefully prior to participation in study, only patients that did not suffer from any systematic disease or any oral pathology were included in the study.

Oral surgery was performed under local anesthesia via a mandibular block of the inferior alveolar nerve and conscious intravenous sedation.

The subjects in the control group underwent the same sensory testing schedule and received a mandibular block anesthesia identical to that administrated to patient on the same day corresponding to the extraction day in the patient group.

The sensory tests included mechanical detection threshold, electrical detection and pain thresholds, thermal detection and pain threshold.

The sensory tests were performed on 5 sites:

within the lingual nerve territory on the anterior two-thirds of the tongue (LNG), within the inferior alveolar nerve territory at the first intact premolar tooth (PM) and at the termination of the nerve (mental nerve territory) located on the skin under the lower lip (MNT).

in the infraorbital nerve territory (maxillary branch of the trigeminal nerve on the skin above the upper lip (UL) and on the skin over the infraorbital foramen On the forarm skin (only in the control group) (FA).

Tests on the face were performed on both the extracted and non extracted sides.

Electrical Detection and Pain Thresholds

Continuous trains of constant current electrical stimuli were delivered to the skin or mucosa through 8-mm diameter spherical gold-plated electrodes spaced 23 mm apart. Stimulus frequency was varied between 10 and 100 Hz with 50% duty cycle. Polarity of the electrodes was randomized. During tongue stimulation the tongue was extended, and dried and isolated by 2×2 inch cotton gauze pads.

Electrical detection and pain thresholds were assessed in the MNT, LNG, lO and UL territories on the extracted and non-extracted sides in the patients and on the injected and non-injected sides and also in the FA, in the control subjects. Detection and pain thresholds were assessed on separate trials by ascending method of limits. Stimulating current was increased slowly until the subject indicated detection or pain. Two detection and pain thresholds were evaluated for both 10 and 100 Hz stimuli for each location.

Data Analysis

Threshold for each modality were evaluated by overall analysis of variance. Planned paired t-tests between the extracted and control sides were performed for each modality. Wilcoxon tests were performed if the data did not meet the normality assumptions required for t-tests.

Results

Brief Summary of Mechanical Detection Threshold and of Thermal Tests

Thermal detection and pain threshold were not altered at any location in patients and no effects were observed in control subjects.

Mechanical detection threshold was reduced in sites innervated by the nerves that were exposed to local inflammation.

Electrical Detection Threshold

FIG. 1. shows the electrical detection thresholds results for all days, groups and frequencies at all tested locations (4 locations in extraction group and 5 locations in control group).

The left panels of FIG. 1 (FIG. 1a and FIG. 1b) show the results for the Extraction Group. Stimulus current in $\mu A$ and standard errors are plotted against days (pre-operative baseline and 2 and 8 days post surgery) for the mental, lingual, coetaneous upper lip and infraorbital nerve territories. In comparison with the control side, the detection thresholds were significantly lower on the extracted side 2 days after surgery in the mental and in the lingual nerve territories at both stimulus frequencies.

The right panels (FIG. 1c and FIG. 1d) show the electrical detection thresholds for the Control Group, receiving a local anesthetic block of the descending mandibular branch of the trigeminal nerve, at the same days and nerve territories as in the Extraction Group with additional tested location in the forearm. In comparison with the control side, no changes are observed in detection thresholds Table 1A and 1B show the same results in a numerical way.

TABLE 1A

Electrical Detection Thresholds of Extraction Group

Extraction Group, 10 Hz

|  | Mental Nerve | | | | Lingual Nerve | | | |
| --- | --- | --- | --- | --- | --- | --- | --- | --- |
|  | Extracted | | Non Extracted | | Extracted | | Non Extracted | |
|  | Mean | S.E. | Mean | S.E. | Mean | S.E. | Mean | S.E. |
| Baseline | 26 | 3 | 24.5 | 3 | 68 | 16 | 65 | 16 |
| 2 P.O.D. | 18.8 | 3 | 27.5 | 2 | 28.5 | 6 | 51.4 | 12 |
| 8 P.O.D. | 27.5 | 3 | 28 | 4 | 34.4 | 6 | 47 | 11 |

|  | Skin Above Upper Lip | | | | Infra Orbital | | | |
| --- | --- | --- | --- | --- | --- | --- | --- | --- |
|  | Extracted | | Non Extracted | | Extracted | | Non Extracted | |
|  | Mean | S.E. | Mean | S.E. | Mean | S.E. | Mean | S.E. |
| Baseline | 24.5 | 4 | 21 | 2 | 22.4 | 2 | 24.8 | 3 |
| 2 P.O.D. | 19.7 | 0.9 | 19 | 3 | 23.2 | 2 | 23.2 | 3 |
| 8 P.O.D. | 23 | 2 | 25.5 | 3 | 30 | 7 | 30.9 | 6 |

TABLE 1A-continued

Electrical Detection Thresholds of Extraction Group

Extraction Group, 100 Hz

|  | Mental Nerve | | | | Linqual Nerve | | | |
| --- | --- | --- | --- | --- | --- | --- | --- | --- |
|  | Extracted | | Non Extracted | | Extracted | | Non Extracted | |
|  | Mean | S.E. | Mean | S.E. | Mean | S.E. | Mean | S.E. |
| Baseline | 28 | 3 | 26.2 | 3 | 71.5 | 13 | 71.8 | 13 |
| 2 P.O.D. | 19.5 | 3 | 26.2 | 2 | 30 | 5 | 65 | 14 |
| 8 P.O.D. | 25.5 | 2 | 22.7 | 2 | 49 | 11 | 44 | 6 |

|  | Skin Above Upper Lip | | | | Infra Orbital | | | |
| --- | --- | --- | --- | --- | --- | --- | --- | --- |
|  | Extracted | | Non Extracted | | Extracted | | Non Extracted | |
|  | Mean | S.E. | Mean | S.E. | Mean | S.E. | Mean | S.E. |
| Baseline | 26.5 | 3 | 27 | 2 | 23.9 | 5 | 27.2 | 7 |
| 2 P.O.D. | 23.7 | 1.5 | 24 | 2 | 21.2 | 2.5 | 18.9 | 2.3 |
| 8 P.O.D. | 23.2 | 2 | 27.4 | 2 | 22.2 | 3 | 22 | 3 |

TABLE 1B

Electrical Detection Thresholds of Control Group

Local Anesthetic Group, 10 Hz (control)

|  | Mental Nerve | | | | Lingual Nerve | | | |
| --- | --- | --- | --- | --- | --- | --- | --- | --- |
|  | Extracted | | Non Extracted | | Extracted | | Non Extracted | |
|  | Mean | S.E. | Mean | S.E. | Mean | S.E. | Mean | S.E. |
| Baseline | 30 | 6.4 | 34 | 7.6 | 80.8 | 25 | 81.3 | 25.2 |
| 2 P.O.D. | 31.7 | 9.4 | 30.8 | 11.6 | 80.5 | 16.5 | 68.3 | 16.4 |
| 8 P.O.D. | 22.2 | 2.7 | 27.1 | 3.5 | 60.8 | 18.4 | 70.5 | 18.6 |

|  | Skin Above Upper Lip | | | | Infra Orbital | | | |
| --- | --- | --- | --- | --- | --- | --- | --- | --- |
|  | Extracted | | Non Extracted | | Extracted | | Non Extracted | |
|  | Mean | S.E. | Mean | S.E. | Mean | S.E. | Mean | S.E. |
| Baseline | 23 | 2.7 | 27.3 | 3.5 | 21.8 | 3.9 | 28.2 | 9.1 |
| 2 P.O.D. | 29.9 | 6.5 | 36.3 | 10.4 | 33.4 | 8.2 | 31.2 | 7.4 |
| 8 P.O.D. | 23.7 | 5.9 | 24.1 | 3.4 | 24.4 | 4.3 | 25.8 | 2.7 |

Local Anesthetic Group, 100 Hz (control)

|  | Mental Nerve | | | | Lingual Nerve | | | |
| --- | --- | --- | --- | --- | --- | --- | --- | --- |
|  | Extracted | | Non Extracted | | Extracted | | Non Extracted | |
|  | Mean | S.E. | Mean | S.E. | Mean | S.E. | Mean | S.E. |
| Baseline | 36.1 | 13.3 | 33.8 | 7.2 | 86.7 | 17.4 | 73.5 | 21.1 |
| 2 P.O.D. | 28.5 | 7.3 | 32.8 | 8.7 | 64.7 | 6.8 | 57.8 | 11.6 |
| 8 P.O.D. | 21.3 | 2.4 | 23 | 4.1 | 53 | 8.6 | 56.1 | 13.3 |

|  | Skin Above Upper Lip | | | | Infra Orbital | | | |
| --- | --- | --- | --- | --- | --- | --- | --- | --- |
|  | Extracted | | Non Extracted | | Extracted | | Non Extracted | |
|  | Mean | S.E. | Mean | S.E. | Mean | S.E. | Mean | S.E. |
| Baseline | 31.7 | 6.1 | 39 | 10.1 | 31.7 | 6.1 | 39 | 10.1 |
| 2 P.O.D. | 34.7 | 9.6 | 38 | 9.3 | 34.7 | 9.6 | 38 | 9.3 |
| 8 P.O.D. | 21.8 | 3.2 | 23.7 | 3.4 | 21.8 | 3.2 | 23.7 | 3.4 | p.o.d. = post operative day
s.e. = standard error
units of results in microampers
no of subjects in trial group = 14, control group (local anesthesic) = 8

Separate analyses of variance and analysis of only the baseline day for both the control and extraction groups showed a significant effect of location, the skin areas (infraorbital, mental and skin above upper lip) being significantly different compared to the lingual territory (oral mucosa), due to decreased sensitivity in the area innervated by the lingual nerve ($p<0.01$). Two days after the extraction the thresholds for detection of electrical stimulation at both frequencies was significantly reduced in comparison to the contralateral control value in the territory of the mental (10 Hz: $18.8\pm3.0$ mA, $27.5\pm2.0$ mA, $p<0.05$; 100 Hz: $19.5\pm3.0$ mA, $26.2\pm2.0$ mA, $p<0.05$) and lingual n(10 Hz: $28.5\pm6.0$ mA, $51.4\pm12.0$ mA, $p<0.05$; 100 Hz: $30.0\pm5.0$ mA, $65.0\pm14.0$ mA, $p<0.05$) nerves but this effect was not evident in the infraorbital nerve area, thus leading to the conclusion that only regions innervated by nerves passing adjacent to the inflammation area, will disclose reduced thresholds for detection of electrical stimulation. No other effects observed at this time in the other nerve territories, or at any location at 8 days after the extraction in either group.

These findings reveal a specific pattern of sensitivity to innocuous and noxious electrical stimuli that indicate inflammatory processes. The territory of the affected mental nerve (inflammation and mechanical trauma) demonstrates a time course of altered sensitivity that can serve as an excellent marker of local or long nerve trunks inflammation. The altered sensitivity in the adjacent lingual nerve (only inflammation) adds magnitude information to this course.

The above results show that inflammatory process with minimal nerve damage along the inferior alveolar and lingual nerves reduced the electrical detection and pain thresholds in the dermatomes innervated by those nerves.

EXPERIMENT 2

Clinical Tests of Electrical Stimulation Thresholds for Detection of Malignancies in the Orofacial Region A pilot trial was designed, aiming to detect changes in electrical stimulation threshold in the orofacial region as a result of soft tissue lesions in this area. Patients with oral lesions suspected with malignancies were included in the pilot study. All patients underwent in addition to complete evaluation of the lesion as needed electrical detection threshold assessment.

The test protocol was as follows:

After a visual macroscopic identification of the lesion, the electrical detection threshold of the branch that innervates the area containing the lesion was checked using the methods of limits.

1. The contralateral area of the same branch was tested as a reference point for comparison.
2. At least one more branch of the trigeminal (5th cranial) nerve that is not related with the area in which the lesion is present, was checked bilaterally.
3. The patient was referred to X ray or CT or MRI as needed.
4. Biopsy was taken as needed.
5. Patients with obvious inflammatory processes due to poor dental situation were excluded or were first referred to dental treatment.

Data Analysis

1. The bilateral ratio was computed in percentages according to the following formula:

Electrical detection threshold of nerve branch in lesion area/Electrical detection threshold in contralateral branch.

The result will be in percentages.

2. A bilateral ratio of 70% or less is considered as indicative for a malignant lesion.

3. The ratios are compared with the pathological and radiological diagnosis.

Results

Eight malignant and 11 benign cases were checked. In 10 of the benign cases the bilateral ratio of the electrical detection threshold was not indicative for malignancy. One case gave a ratio of 37% in the lingual area for a lesion described as "speckled red white lesion on anterior left floor of the mouth", the pathologic answer being "no malignancy, some atypical cells". This sample of benign lesions resulted in one false positive result.

All the eight malignant cases were detected by bilateral ratio of 70% or below, the average ratio being 56.83% for the branches related with the affected area, versus 99.25% for the branch innervating the non affected side. Interestingly, in two cases with lingual malignant lesion, the ratio for the mental nerve was also indicative for malignancy, while the CT and other radiographic analyses were negative. In one case, during the surgery, it became evident that the lesion has affected the lingual mandibular periost, while in the second case MRI examination revealed close contact of the tumor with the mandible. In both cases no bone erosion was present at the time of the examination, thus preventing conventional radiographic methods to detect the extent of involvement of the tumor.

Figure 2:
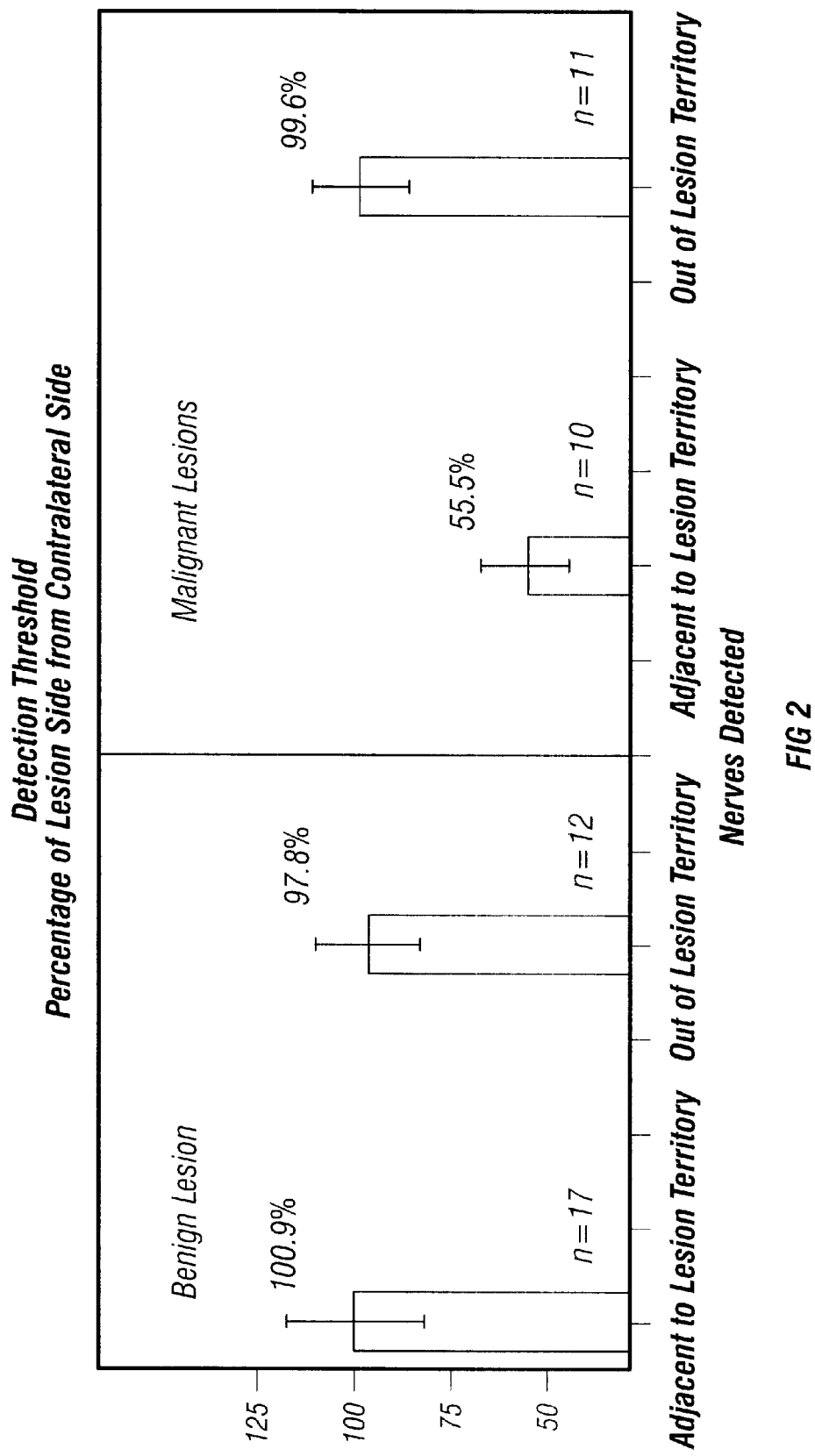

The test results are summarized in Tables 2a and 2b and are represented graphically in FIG. 2.

The above results show clearly that malignancy lesions cause changes in the electrical detection thresholds while benign lesions do not cause such changes.

TABLE 2a

The bilateral ratio of Electrical Detection Threshold for Malignant tumors

| Case No. | Nerve | Detection Threshold in lesion side/ Detection Threshold in contralateral side (%) | |
|---|---|---|---|
| | | In lesion territory | Out of lesion territory |
| 1 | Mental | 59.429825 | |
| | Lingual | 70.549085 | |
| | Infraorbital | | 108.6330935 |
| 2 | Mental | 54.62963 | |
| | Lingual | 58.201058 | |
| | Infraorbital | | 103.3333333 |
| 3 | Mental | | 106.3829787 |
| | Lingual | 49.094567 | |
| | Infraorbital | | 108.6206897 |
| 4 | Mental | 55.612245 | |
| | Lingual | | 83.97435897 |
| | Infraorbital | | 99.12663755 |
| 5 | Mental | | 103.4562212 |
| | Lingual | 61.071429 | |
| | Infraorbital | | 85.16129032 |
| 6 | Mental | 79.827089 | |
| | Lingual | 53.579176 | |
| | Infraorbital | | 101.2145749 |
| 7 | Mental | 59.816754 | |
| | Lingual | | |
| | Infraorbital | | 108.3333333 |
| 9 | Mental | 20.707733 | |
| | Lingual | 59.441708 | |
| | Infraorbital | | 83.53413655 |
| | AVERAGE | 56.830025 | 99.2518771 |
| | SD | 13.951205 | 10.13066905 |

TABLE 2b

The bilateral ratio of Electrical Detection Threshold For Benign cases

| Case No. | Nerve | Detection Threshold in lesion side/ Detection Threshold in contralateral side (%) | |
|---|---|---|---|
| | | In lesion territory | Out of lesion territory |
| 1 | Mental | 103.62173 | |
| | Lingual | 81.467181 | |
| | Infraorbital | | 111.0795455 |
| | | | 93.7007874 |
| 2 | Mental | | 99.15433404 |
| | Lingual | 97.678019 | |
| | Infraorbital | | |
| 3 | Mental | | 99.15433404 |
| | Lingual | 97.678019 | |
| | Infraorbital | | |
| 4 | Mental | | |
| | Lingual | 93.333333 | |
| | Infraorbital | | |
| 5 | Mental | 123.73626 | |
| | Lingual | | |
| | Infraorbital | | |
| 6 | Mental | 114.51613 | |
| | Lingual | | 81.66666667 |
| | Infraorbital | | 108.1218274 |
| 7 | Mental | 111.16751 | |
| | Lingual | | 86.75496689 |
| | Infraorbital | | 83.25791855 |
| 8 | Mental | | 92.51870324 |
| | Lingual | 133.33333 | |
| | Infraorbital | | 86.19047619 |
| 9 | Mental | 88.557214 | |
| | Lingual | | |
| | Infraorbital | | |
| 10 | Mental | | |
| | Lingual | 95.604396 | |
| | Infraorbital | | |
| | AVERAGE | 103.69938 | 94.15995599 |
| | SD | 15.561112 | 10.1504335 |

There is accumulating evidence from recent studies that malignancy causes sensory changes and that in many cases, neurological symptoms precede cancer diagnosis. For example, the results of a nationwide survey on paraneoplastic neurological syndrome, that was carried out in Japan, showed that neurological symptoms preceded diagnosis of malignancy in over 83% of examined cases (Rinsho Shinkerigaku *Project group on paraneoplastic neurological syndromes, Neuroimmunological Disease Research Committee, The Ministry of Health and Welfare, Japan,* Febuary 37(2), (1997) p.93–98); Hughes et al. showed that cancer caused peripheral neuropathy (Hughes et al. *J Neurol.* 243 (1996) p. 371–376) and in another study, various paraneoplastic neurological syndromes have been described in association with small cell lung cancer (Khouatra et al, *Rev. Med. Interne* 18, (1997) p. 652–656). Those phenomena should be categorized as paraneoplastic syndrome or polyneuropathy due to a neoplastic condition.

By contrast, combining our above disclosed results in humans, with the above mentioned evidence for the existence of local inflammatory processes, still with no clinical manifestation but that can be demonstrated by the evoked effect of electrical stimulation, from the very first stage of malignancy and we come with the present invention—a diagnostic tool for localized malignancies in their very first stages based on the detection of sensory changes in the peripheral nervous system.

The sensory changes are detected in one of two following ways or by both:

(a) by measuring and comparing the detection thresholds for electrical stimulation in the vicinity of a suspected site and in its homological contralateral site.

(b) by measuring the difference between the detection thresholds for electrical stimulation in two different nerve territories and re-measuring the said difference after, at least, one time interval.

A difference of more than 20% between the two corresponding thresholds of (a) or a change of more than 20% in the difference described in (b), indicates a higher probability of malignancy and/or inflammatory process.

Measuring the detection threshold for electrical stimulation is done by the following steps:

1) Attaching electrodes that are connected to an electrical pulse generator, at a distance from 0.1 mm to the maximal size of the dermatome innervated by the tested nerve (preferably at a distance of 0.3–5 cm), to the tested location in the subject's body.

2) Applying a train of electrical pulses of varying intensities in the range of 1 $\mu$A to 1 A, in accordance with any of the known in the art protocols for threshold measurements and collecting the subject's responses to the stimulation.

3) processing this data in accordance with the chosen protocol to obtain the electrical detection threshold.

The electrodes attached to skin or mucosa can be of any type suitable for applying electrical stimulation. They can take the form of metal discs at the face of an insulator by using wires truncated at the face. They can be of any shape and their surface can be metallic or non-metallic. Alternatively the electrodes can comprise an electrolytic cell coupled to the skin or mucosa by a salt bridge in the form of an electrolyte containing gel or sponge or porous plug which can be used with a metal electrode also.

The apparatus for measuring the threshold to electrical stimulation can be of the kind disclosed in U.S. Pat. Nos. 5,191,896 or in 4,338,945.

The threshold (steps 2 and 3 above) can be measured by any known in the art protocols such as: a multiple random staircase method (Gracely et. al. *Pain* 32, (1988) p. 55–63), method of limits or method of levels (Yarnitski D. and Ochoa J. L. *Pain* 40, (1990) p. 85–91), forced choice method (Jamal, G. A. et al, *J Neurol Neurosurg Psychiatry* 48, (1985) p. 354–360), thermal sensitivity limen (Xavier Navarro and William R. Kennedy *J. Neurol Neurosurg Psychiatry* 54,(1991) p. 60–64), method of suprathreshold (Price D. D., *Psychological and Neural Mechanisms of Pain,* (1988) p. 18–49) and the protocols disclosed in U.S. Pat. No. 5,191,896.

The method according to the present invention is useful for the diagnosis of different primary malignancies such as:

a) Basal cell carcinoma, squamous cell carcinoma, malignant melanoma or other malignancy of the skin or mucosa when the electrical stimulation is performed on the skin or mucosa adjacent to suspected lesion b) Malignancies of the oral cavity when the test is performed on the oral mucosa in an area adjacent to the suspected lesion or in area innervated by nerve adjacent to the lesion.

c) Malignancies of the gastro intestinal tract when the test is performed on the mucosa adjacent to lesion suspected in malignancy.

d) Malignancies of other mucosas, such as of the cervix uteri, when the test is performed on the mucosa adjacent to lesion suspected in malignancy.

e) Breast malignancies when the test is performed on the nipples or the breast skin.

f) Bone malignancies when the test is performed on the adjacent skin.

Furthermore, the method according to the present invention is useful for the diagnosis of stress fractures in the limbs of humans, racing horses and racing dogs when the test is performed on the skin adjacent to suspected area, wherein the human response to the stimulation is yes/no as described above and wherein the animal's response to stimulation is considered positive when it lifts up its tested leg in response to the electrical stimulation.

What is claimed is:

1. A method useful for the detection of inflammatory processes and malignancies in the human body comprising;
    a) measuring the detection threshold for electrical stimulation in a suspected location in a human body;
    b) measuring the detection threshold for electrical stimulation in the homological contralateral location to the suspected location;
    c) calculating the difference between the two thresholds of the two tested locations wherein a difference bigger than 20% indicates higher probability of pathology.

2. A method according to claim 1 wherein the detection thresholds are measured by:
    a) attaching electrodes that are connected to an electrical pulse generator, to the tested location, at a predetermined distance apart;
    b) applying electrical stimulation through said electrodes;
    c) collecting patient's responses to electrical stimulation;
    d) analyzing the collected data to obtain the said detection threshold.

3. A method according to claim 2 wherein the electrodes are applied to the skin.

4. A method according to claim 2 wherein the electrodes are applied to mucosa wherein tested region is dried and isolated with cotton gauze pads.

5. A method according to claim 2 wherein the electrical stimulation is a train of electrical pulses of varied intensities in the range 1 $\mu$A to 1 A.

6. A method according to claim 2 wherein steps b and c are done in accordance with any known protocol for obtaining detection threshold for electrical stimulation.

7. A method according to claim 6 wherein said protocol is selected from a multiple random staircase method, a method of limits, a method of forced choice, a method of suprathreshold and a thermal sensitivity limen.

8. A method according to claim 1 useful for the detection of Basal cell or squamous cell carcinoma or malignant melanoma or other malignancy of the skin when the electrical stimulation is performed on the skin adjacent to suspected lesion; or for the detection of malignancies of the oral cavity when the electrical stimulation is performed on the oral mucosa in an area adjacent to the suspected lesion or in area innervated by nerve adjacent to the lesion; or for the detection of malignancies of the gastro intestinal tract when the electrical stimulation is performed on the mucosa adjacent to lesion suspected in malignancy; or for the detection of malignancies of other mucosas, such as of the cervix uteri, when the test is performed on the mucosa adjacent to lesion suspected in malignancy; or for the detection of breast cancer when the electrical stimulation is performed on the nipples or breast skin; or for the detection of bone malignancies when the electrical stimulation is performed on the adjacent skin.

9. A method according to claim 2 wherein the electrodes are of any type suitable for applying electrical stimulation.

10. A method according to claim 2 wherein the electrodes can be of any shape and wherein their surface can be metallic or non-metallic, or in the form of metal discs at the face of an insulator by using wires truncated at the face, or alternatively the electrodes can comprise an electrolytic cell coupled to the skin or mucosa by a salt bridge in the form of an electrolyte containing gel or sponge or porous plug which can be used with a metal electrode also.

11. A method according to claim 2 wherein the distance between the electrodes is in the range from 0.1 mm to the maximal size of the dermatome innervated by the tested nerve.

12. A method according to claim 1 useful for the detection of inflammatory processes in bones or joints when the electrical stimulation is performed on the skin adjacent to suspected area.

13. A method according to claim 1 useful for the detection of stress fractures in human legs when the electrical stimulation is performed on the skin adjacent to suspected area.

* * * * *